United States Patent [19]

Müller et al.

[11] 4,171,324

[45] Oct. 16, 1979

[54] PREPARATION OF SODIUM ALLYL AND METHALLYL SULFONATE

[75] Inventors: Dieter J. Müller; Wilhelm Knepper, both of Marl, Fed. Rep. of Germany

[73] Assignee: Chemische Werke Huels Aktiengesellschaft, Marl, Fed. Rep. of Germany

[21] Appl. No.: 813,011

[22] Filed: Jul. 5, 1977

[30] Foreign Application Priority Data

Jul. 6, 1976 [DE] Fed. Rep. of Germany ....... 2630238
May 6, 1977 [DE] Fed. Rep. of Germany ....... 2720346

[51] Int. Cl.$^2$ ........................................... C07C 143/72
[52] U.S. Cl. ................................................ 260/513 B
[58] Field of Search ..................................... 260/513 B

[56] References Cited

U.S. PATENT DOCUMENTS

| | | | |
|---|---|---|---|
| 2,653,970 | 9/1953 | Fessler | 260/513 B |
| 3,168,555 | 2/1965 | Clippinger | 260/513 B |
| 3,453,320 | 7/1969 | Robeson | 260/513 B |
| 3,755,430 | 8/1973 | Lorenz | 260/513 B |

*Primary Examiner*—Alan Siegel
*Attorney, Agent, or Firm*—Millen & White

[57] ABSTRACT

An improved process for the conversion of allyl and methallyl chloride to sodium allyl and methallyl sulfonate, respectively, by reaction with aqueous sodium sulfite which comprises conducting the reaction at 33°–70° C. and 33°–80° C., respectively, while maintaining the pH at 7–11 throughout the reaction.

9 Claims, 1 Drawing Figure

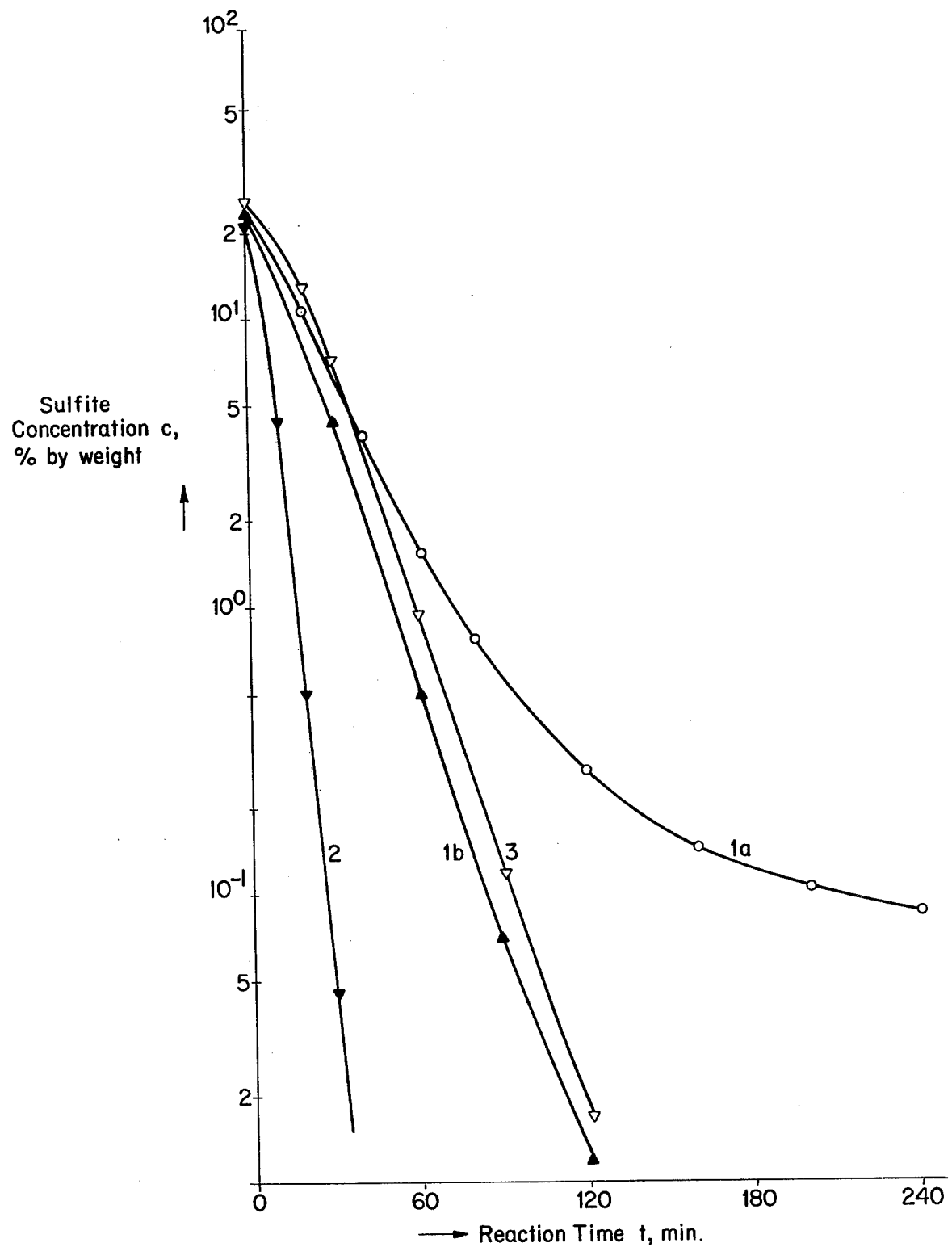

4,171,324

PREPARATION OF SODIUM ALLYL AND METHALLYL SULFONATE

BACKGROUND OF THE INVENTION

This invention relates to a process for the preparation of sodium allyl sulfonate (AS) and sodium methallyl sulfonate (MAS) employing aqueous sodium sulfite solutions in an emulsion.

Sodium allyl and methallyl sulfonate are, along with other unsaturated sulfonates, important comonomers for the copolymerization with other unsaturated monomers, especially with acrylonitrile.

Sodium allyl sulfonate is produced in general by the reaction of allyl chloride with sodium sulfite in an aqueous and/or aqueous-alcoholic solution in accordance with the following reaction equation:

$$CH_2=CH-CH_2Cl + Na_2SO_3 \xrightarrow{H_2O/C_2H_5OH} CH_2=CH-CH_2SO_3Na + NaCl$$

The reaction is preferably conducted in an aqueous-ethanolic solution in the boiling temperature range of 42°–44° C. under agitation and reflux.

However, such a process gives low yields due to considerable hydrolysis and solvolysis reactions. Therefore, the selectivity of the reaction is extremely unsatisfactory. Furthermore, such a process has low space-time yields. In accordance with U.S. Pat. No. 2,601,256, reaction times of 12 hours are required. Since the solubility of $Na_2SO_3$ in water-alcohol mixtures is low, relatively dilute reaction solutions are furthermore obtained, the working-up of which requires high evaporation costs.

Although a higher selectivity is provided by the processes of East German Pat. Nos. 70 086 and 106,828, according to which allyl chloride is introduced in the gaseous phase into an aqueous $Na_2SO_3$ solution at, for example, 50° C., wherein part of the allyl chloride is reacted and another part escapes in the unreacted state from the reaction solution and is recycled after intermediate condensation and re-evaporation, these processes exhibit a higher energy consumption as a result of the continuous evaporation and condensation. Furthermore, they require relatively long reaction periods in consequence of the poor mass transfer through the interface from the gaseous to the liquid phase.

In general, the reaction solutions are worked up, in order to obtain the sodium allyl sulfonate in the pure state, by evaporation of the solution, extraction of the AS with alcohol, and subsequent crystallization from alcohol to obtain the compound in the pure form.

There is thus lacking in the prior art a process which makes possible the production of sodium allyl sulfonate by the reaction of allyl chloride in maximally concentrated $Na_2SO_3$ solutions in a maximally short reaction time and with high selectivity and low energy consumption.

The commercial production of MAS is conducted either at temperatures of 30°–70° C., preferably 65°–66° G., in accordance with the following reaction equation:

$$CH_2=\overset{CH_3}{\underset{|}{C}}-CH_2Cl + Na_2SO_3 \longrightarrow$$

-continued
$$CH_2=\overset{CH_3}{\underset{|}{C}}-CH_2-SO_3Na + NaCl$$

or by sulfonation of isobutene with organic $SO_3$ complex compounds in preferably inert solvents, especially halogenated hydrocarbons.

The latter method is commercially inadequate, since, on the one hand, the resultant salt has an unsatisfactory degree of purity (at most 97%) and, on the other hand, the solvent as well as the relatively expensive complexing agents must be separated from the sulfonic acid after the reaction in expensive recovery processes. In this connection, the recovery rate of the complexing agents is only about 90%, and the selectivity, based on the $SO_3$ conversion, is at best 95%. Due to the fact that the primarily formed sulfonic acid has a great tendency to decompose, this acid cannot be isolated as such and therefore can be worked up only after neutralization to form its salt.

In accordance with the first-mentioned conventional process, aqueous $Na_2SO_3$ solutions are normally reacted with a stoichiometric excess of MAC with the addition of solubilizers (U.S. Pat. No. 2,601,256) or emulsifiers (German Published Application DAS 1,804,135). However, it is also possible, on the other hand, to employ a quantity of MAC which is less than the stoichiometric amount, as set forth in U.S. Pat. No. 3,453,320, whereby the separation of NaCl is said to be facilitated. The yields of MAS according to these methods are only about 75% to 85%, based on the component added in less than stoichiometric amount, with reaction times of 2–12 hours.

It is also possible, as disclosed in East German Pat. Nos. 70,086 and 106,828, to introduce the MAC required for the reaction in the gaseous form in metered amounts into an aqueous $Na_2SO_3$ solution without the addition of auxiliary agents at temperatures of above the MAC boiling point. Because of the poor mass transfer from the gaseous to the liquid phase, a portion of the thus-introduced MAC is discharged from the reactor in unreacted form, so that energy-consuming intermediate condensation and revaporization stages are required to recycle the MAC. Moreover, this process requires relatively long reaction times.

All of the aforementioned processes of reacting MAC with $Na_2SO_3$ also have the general disadvantage that saturated sulfonates, in part polymeric and/or oligomeric MAS, are produced in addition to the desired, unsaturated sulfonate. These saturated sulfonates are practically inseparable from the MAS by conventional working-up methods, e.g., fractional crystallization or extraction, due to the fact that their characteristics are similar to those of MAS.

Consequently, there is the need for a process which permits the production of MAS by reacting MAC with an aqueous $Na_2SO_3$ solution in a maximally short reaction time with high selectivity, without the formation of saturated sulfonates.

SUMMARY OF THE INVENTION

This invention relates to a process for the production of sodium allyl sulfonate and sodium methallyl sulfonate by adding a stoichiometric excess of 10–40% of allyl chloride or methallyl chloride to an aqueous $Na_2SO_3$ solution at a temperature of 33°–70° C., in the case of allyl chloride, and 33°–80° C., in the case of methallyl chloride and continuing the reaction while subjecting the reaction mixture to vigorous agitation and under a pressure of 1.0–2.3 bar, while maintaining a pH of 7–11, preferably 9–10, by the addition of sodium hydroxide to the reaction mixture, until the $Na_2SO_3$ is substantially completely consumed.

DETAILED DISCUSSION

These reactions are preferably conducted under an atmosphere of a protective gas, for example nitrogen.

The reaction is conducted throughout at 33°–70° C., in the case of allyl chloride and 33°–80° C., in the case of methallyl chloride.

In the conventional processes, the unavoidable hydrolysis of the allyl chloride or methallyl chloride, which takes place simultaneously with the AS or MAS formation, is not taken into account. The hydrochloric acid formed by the hydrolysis lowers the pH of the starting solution during the course of the reaction to about 4 in the case of allyl chloride and about 3–4 in the case of methallyl chloride. At these low pH values, the reaction progresses at a considerably lower rate. In the case of methallyl chloride, the reaction substantially terminates at a pH of <4, although residual sulfite remains. To avoid this decrease in the reaction velocity, it is necessary, after initially adjusting the pH to 7–11, to maintain this same pH range, preferably 9–11, during the reaction, by the metered addition of sodium hydroxide, preferably as an aqueous solution. During the metered addition of the sodium hydroxide, care must be taken that a pH of 11 is not exceeded, since the hydrolysis of the allyl chloride increases precipitiously at pH values of above 11, and the selectivity of the reaction is correspondingly lowered. Moreover in so doing surprisingly the formation of saturated sulfonates is practically entirely suppressed throughout the reaction.

The aqueous $Na_2SO_3$ solutions are preferably employed as saturated solutions. The use of $Na_2SO_3$ suspensions and/or the precipitation of $Na_2SO_3$ during the reaction, for example by too rapid an increase in the reaction temperature, is to be avoided as far as possible, since this would result in disturbances and delays in the progress of the reaction. The solubility of $Na_2SO_3$ in water reaches a maximum at 33° C. with 28%. With a rising temperature, the solubility decreases again and is down to 23.5% at 70° C. and down to 22.3% at 80° C. It is therefore preferred to utilize $Na_2SO_3$ solutions having a concentration of 23.5–28%, in the case of allyl chloride, and of 22.3–28%, in the case of methallyl chloride.

A technically significant temperature is about 44° C., in the case of allyl chloride, and 65°–66° C., in the case of methallyl chloride. This is the boiling point of the thus-formed azeotrope of allyl chloride and water and methallyl chloride and water, respectively, under normal pressure. Reactions above this temperature must, therefore, be conducted under pressure. From the dependency of vapor pressure of the azetrope above the reaction solution as a function of the temperature, in the case of allyl chloride, a pressure of, for example, 1.3 bar is required for a desired reaction temperature of 50° C.; 1.8 bar for 60° C.; and 2.25 bar for 70° C. In the case of methallyl chloride, a pressure of at least 1.9 bar is required for a desired reaction temperature of 80° C. Although it is possible to employ higher reaction temperatures by further increasing the pressure, this is unnecessary since the reaction rate is adequate in the preferred temperature ranges. For example, the reaction time of allyl chloride at 45° C. is about 240 minutes; at 50° C., about 155 minutes; at 60° C., about 75 minutes; and at 70° C., about 40 minutes. In the case of methallyl chloride, the reaction time at 65°–66° C. is about 100 minutes and at 80° C., about 30 minutes.

Moreover, with an increasing temperature, the amount of hydrolyzed allyl chloride increases, in spite of the shorter total reaction time, from, for example, 0.3% at 36° C. to 1.4% at 70° C., and the amount of hydrolyzed methallyl chloride increases from, for example, 0.4% at 60° C. to 0.9% at 80° C. Therefore, a further increase in temperature excessively reduces the selectivity of the reaction.

The reaction of allyl chloride and methallyl chloride with $Na_2SO_3$ is exothermic. Therefore, they advantageously are added to a sulfite solution which has been preheated to a temperature which is somewhat lower than the desired reaction temperature. The starting temperature is dependent on the heat flow balance for the reaction and the technical plant. In the simplest case, a temperature below 65° C., e.g., about 44° C., in the case of allyl chloride, is selected for the starting temperature, so that it is possible to add the allyl or methallyl chloride under normal pressure. This mode of operation is energy-preserving in two respects, viz., on the one hand, at least a portion of the heat of reaction is utilized to heat the reaction mixture, and on the other hand, with a lower starting temperature, higher initial $Na_2SO_3$ concentrations can be employed so that reaction solutions of higher concentrations are obtained, thereby reducing evaporating expenses after completion of the reaction. After startup of the reaction, the reaction temperature rises to the desired temperature, e.g., between 45° and 70° C., in the case of allyl chloride, which, in correspondence with the predetermined operating pressure, is limited to the boiling point of the reaction mixture. If the operating pressure corresponds to the vapor pressure of the azeotrope at the desired reaction temperature, the heat liberated during the continuing reaction can be readily removed by evaporation cooling and reflux condensation.

Conducting the reaction under a slight excess pressure is also advantageous in that, after termination of the reaction, the excess organic phase can be extensively removed by distillation solely by reduction of the pressure, without supplying additional energy. The organic phase can be reused.

Thus, a reaction temperature, preferably of 45° to 70° C., especially 50° to 60° C., is employed in the case of allyl chloride.

The process of this invention makes possible the production of allyl sulfonate and methallyl sulfonate employing aqueous $Na_2SO_3$ solutions with practically complete $Na_2SO_3$ conversion, with the desired sulfonate product being obtained as a highly concentrated aqueous solution, viz., about 23.5% to 27.3%, in the case of allyl chloride, and 24.0 to 28.6%, in the case of methallyl chloride, containing NaCl. From these solutions, residual allyl chloride or methallyl chloride can be isolated in the pure state according to conventional methods. By the process of this invention, extremely short reaction times with complete sulfite conversion and a minimum formation of by-products are achieved. The hydrolysis of the allyl chloride and methallyl chloride ranges, depending on the selected reaction temperature, from 0.3% to at most 1.4%, in the case of allyl chloride and from 0.3% to at most 0.9%, in the case of methallyl chloride, calculated on the amount thereof initially employed.

In the process of this invention, allyl or methallyl chloride is added in a stoichiometric excess of 10–40% to an aqueous sodium sulfite solution, preheated to the desired starting or reaction temperature, which preferably is saturated at this temperature and has a pH of 7–11, preferably 9–10.

The allyl or methallyl chloride can be added under normal pressure at starting temperatures of up to 44° C. in the case of the former and up to 65° C. in the case of the latter. Above this temperature, the compound is added by way of a pressure charging valve.

With thorough agitation, a finely dispersed emulsion is obtained which optionally can be stabilized by the addition of emulsifiers.

The heat of reaction evolving in the initial stage of the reaction serves for the continued heating of the reaction mixture from the starting temperature to the desired reaction temperature which preferably is 45° to 70° C., especially 50°–60° C., in the case of allyl chloride and 60°–70° C., in the case of methallyl chloride. A temperature rise beyond the desired reaction temperature is avoided by establishing a predetermined operating pressure, preferably between 1.3 and 1.8 bar in the case of allyl chloride, in accordance with the vapor pressure of the thus-formed azeotrope. The amount of heat of reaction produced above and beyond this amount can be removed by evaporative cooling and reflux condensation of the organic phase.

During the reaction, aqueous NaOH solution is added in metered amounts so that a pH of 7–11, preferably 9–10, is maintained. The reaction is terminated once the sulfite content in the aqueous phase of the reaction mixture has dropped to $\leq 0.03\%$. As will be apparent to those skilled in the art, other alkaline sodium salts, e.g., sodium carbonate, can be employed.

The excess organic phase is initially driven over by distillation merely on account of pressure reduction; any residual organic phase can optionally be removed by an external source of energy. The thus-recovered allyl chloride or methallyl chloride, respectively, is advantageously reused.

The remaining aqueous reaction solution, consisting essentiall of sodium allyl sulfonate and sodium methallyl sulfonate, respectively, and NaCl, is evaporated and extracted, for example, in accordance with the conventional working-up methods, in order to isolate the sulfonate therefrom in the pure form.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

For the following experiments (Examples 1, 1a and 2), an agitator-equipped apparatus is used which is to be operated under pressure and comprises a reflux condenser, this apparatus permitting temperature control by thermostat and pH value control with the feature of maintaining the pH value automatically constant by the metered addition of aqueous NaOH. Nitrogen serves as the protective gas atmosphere.

The reactor is charged with 2,500 g. of aqueous $Na_2SO_3$ solution, the concentration of which corresponds approximately to the saturation concentration at the desired reaction temperature. After heating to the reaction temperature and setting a pH of about 9.5, allyl chloride is added under agitation in a stoichiometric excess of 20%. At above 44° C. allyl chloride is introduced under pressure, and the reaction is conducted under pressure.

The reaction between allyl chloride and $Na_2SO_3$, conducted with intensive agitation, is followed by taking samples and determining the $Na_2SO_3$ in the aqueous phase as a function of the time. The reaction is terminated once the $Na_2SO_3$ content has dropped to about 0.03%.

During the reaction, the pH of about 9.5 is maintained constant by the metered addition of 1 N NaOH. From the consumption, the thus-hydrolyzed amount of allyl chloride can be calculated. The reaction mixture obtained after termination of the reaction is freed of the excess organic phase and subsequently the chloride content is determined in the aqueous phase by argentometry and the allyl sulfonate content is determined by bromometry. The allyl sulfonate content can also be determined, for control purposes, indirectly from the total chloride content minus the chloride content from the hydrolysis reaction.

It is moreover possible to calculate the allyl sulfonate content to be expected theoretically under consideration of the hydrolysis dilution and the NaOH addition. The results of this series of experiments are compiled in Table 1.

Selectivities of $\geq 99\%$ are obtained for reaction temperatures of up to 60° C. from the amount of allyl chloride reacted in total and the amount of allyl chloride which is hydrolyzed, taking into account the good correspondence between the allyl sulfonate contents to be theoretically expected and the allyl sulfonate contents found analytically.

COMPARATIVE EXAMPLE 1a

The process is conducted as set forth in Example 1 at the reaction temperature of 44° C., except the initially set pH value of 9.5 is not maintained constant by the addition of NaOH. During the course of the reaction, the pH value drops and reaches, for example after a reaction time of 240 minutes, a value of 5.3, and after 330 minutes, a value of 4.1. In spite of a considerably longer reaction time of up to 330 minutes, the desired final $Na_2SO_3$ content of 0.03% is not attained.

EXAMPLE 2

The process is conducted analogously to Example 1, but a lower starting temperature (44° C.) is selected, and after the addition of the allyl chloride the temperature is raised to 60° C. utilizing both the heat of reaction and with additional energy being supplied. The temperature elevation must only take place so rapidly that during the heating to 60° C. there occur no reaction-delaying precipitations by an oversaturation of $Na_2SO_3$. A time of 10 minutes is sufficient. After reaching 60° C., the reaction is conducted as set forth in Example 1.

By means of this mode of operation, high allyl sulfonate concentrations are obtained in the reaction solution, as they are otherwise obtained in the isothermic process at 44° C. in Example 1. However, the long reaction times required in case of the isothermic procedure are unnecessary.

Table 1 contains the result.

TABLE 1

Results of Experiments Set Forth in Examples 1, 1a, and 2

| Example | Na$_2$SO$_3$ Charged 2,500 g. Content % by Wt. | Starting Temp. °C. | Reaction Temp. °C. | Operating Pressure bar | Amount of Allyl Chloride Starting Material g. | Reaction Time to 0.03% Na$_2$SO$_3$ min. | Hydrolyzed Proportion Allyl Chloride % | Na Allyl Sulfonate Content in Reaction Solution, % | | |
|---|---|---|---|---|---|---|---|---|---|---|
| | | | | | | | | Bromo-metry | From NaCl Content | Theoret. (Hydrol. Taken into Acc.) |
| 1 | 27.5 | 36 | 36 | 1 | 501 | 490 | 0.3 | 26.6 | 26.4 | 26.76 |
| | 26.5 | 44 | 44 | 1 | 483 | 240 | 0.4 | 25.9 | 26.2 | 25.87 |
| | 25.7 | 50 | 50 | 1.3 | 468 | 155 | 0.55 | 25.2 | 25.1 | 25.11 |
| | 24.5 | 60 | 60 | 1.8 | 446 | 75 | 0.85 | 24.5 | 24.1 | 23.94 |
| | 23.4 | 70 | 70 | 2.3 | 426 | 40 | 1.4 | 22.6 | 22.6 | 22.77 |
| 1a | 26.5 | 44 | 44 | 1 | 483 | >330 | 0.4 | 25.7 | — | 26.11 |
| 2 | 26.5 | 44 | 60 | 1.8 | 483 | 85 | 0.85 | 25.8 | 25.7 | 25.87 |

COMPARATIVE EXAMPLE 3a

For the following experiments (Examples 3a, 3b, 4 and 5) an agitator-equipped apparatus with reflux condenser is used, which is to be operated under pressure and which permits temperature control by thermostat and pH control, maintaining the pH value constant by the metered addition of aqueous NaOH. Nitrogen serves as the protective gas atmosphere.

In the agitator-equipped apparatus, 2,500 g. of a 24% Na$_2$SO$_3$ solution is provided, this solution being saturated at the desired reaction temperature of 65°-66° C. and having a pH of 9.5. To this solution is added 517 g. of MAC, and the reaction is conducted in the thus-produced emulsion under intense dispersion at the thus-obtained boiling temperature of 65°-66° C.

The progress of the reaction with MAS formation, which is equivalent to the decrease in the Na$_2$SO$_3$ concentration, is observed by taking samples and determining the sulfite content in the aqueous phase of the emulsion. The resultant decrease in the Na$_2$SO$_3$ concentration is illustrated in FIG. 1, curve 1a. The reaction is terminated after 240 minutes, because the reaction has practically stopped at a sulfite content of 0.09%. In the meantime, the pH has dropped to 3.8. The excess organic phase is removed by distillation. The aqueous solution contains about 25.2% MAS. The content of saturated sulfonates is determined, after a gentle vacuum evaporation of the solution to dryness, to be 1.0%, based on the dry substance. This corresponds to a concentration of saturated sulfonates of about 0.35% in the aqueous reaction solution.

EXAMPLE 3b

The procedure of Comparative Example 3a is employed, except that the HCl produced by MAC hydrolysis is neutralized by the continuous metered addition of 1 N NaOH so that the pH value of 9.5 is kept constant. By an automatic recordation of the NaOH consumption, the course of the hydrolysis and the thus-hydrolyzed proportion of MAC up to the end of the reaction can be determined.

The progress of the reaction is observed, as set forth in Experiment 3a, by taking samples and sulfite determination. The reaction is considered terminated once the sulfite content has decreased to ≦0.03%. The result is shown in FIG. 1, curve 1b.

The proportion of hydrolyzed MAC is around 0.6% at the end of the reaction. The aqueous reaction solution contains about 25.3% of MAS and no saturated sulfonates.

EXAMPLE 4

The agitator-equipped apparatus is charged with 2,691 g. of a 22.3% Na$_2$SO$_3$ solution at 80° C.; the pH of this solution is 9.5. Under pressure, 517 g. of MAC is added to this solution, and the reaction is conducted under a pressure of 1.9-2.0 bar.

Otherwise, the procedure of Example 3b is followed. The result is shown in FIG. 1, curve 2.

The proportion of hydrolyzed MAC is, at the end of the reaction, 0.9%. The aqueous solution contains about 23.6% of MAS and no saturated sulfonates.

EXAMPLE 5

In the agitator-equipped apparatus, 2,273 g. of a 26.4% Na$_2$SO$_3$ solution is provided, having a pH of 9.5, at a starting temperature of 45° C. To this solution is added 517 g. of MAC, and the temperature is elevated, with the use of the heat of reaction, to 65°-66° C. within 20 minutes, without the occurrence of any precipitations in the meantime.

Otherwise, the procedure is the same as set forth in Example 3b. The result is shown in FIG. 1, curve 3.

The proportion of hydrolyzed MAC is 0.6%. The aqueous solution contains about 27.4% of MAS and no saturated sulfonates.

With the use of this variation of the process, a more concentrated reaction solution is obtained, while the reaction time is only slightly prolonged, with utilization of the heat of reaction. Such reaction solutions are advantageous on account of the lower costs for the evaporation during the subsequent working-up procedure.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. In a process for the production of sodium allyl sulfonate and sodium methallyl sulfonate by the reaction of allyl chloride and methallyl chloride respectively, with aqueous Na$_2$SO$_3$, the improvement which comprises adding the allyl or methallyl chloride in a 10-40% stoichiometric excess and with vigorous mixing to an aqueous Na$_2$SO$_3$ solution, at a temperature of 33°-70° C.; in the case of allyl chloride, and 33°-80° C., in the case of methallyl chloride, and conducting the reaction at a pressure of 1.0–2.3 bar while maintaining the pH of the reaction mixture at 7–11 by the addition of sodium hydroxide, until consumption of $Na_2SO_3$ is substantially complete.

2. A process according to claim 1, wherein the pH of the reaction mixture is maintained at 9–10 by the metered addition of aqueous sodium hydroxide thereto.

3. A process according to claim 1, wherein allyl chloride and a $Na_2SO_3$ solution with a $Na_2SO_3$ content of from 28%, at a starting temperature of 33° C., to 23.5%, at a starting temperature of 70° C., are employed.

4. A process according to claim 3, wherein a starting temperature of about 44° C. is employed, a reaction temperature of 50°–60° C. is employed, which temperature is reached utilizing the heat of reaction.

5. A process according to claim 3, wherein the reaction is initiated at ambient pressure and thereafter is conducted at a pressure of from 1 to 2.3 bar.

6. A process according to claim 5, wherein the reaction is conducted at a pressure of 1.3 to 1.8 bar.

7. A process according to claim 1, wherein methallyl chloride and a $Na_2SO_3$ solution with a $Na_2SO_3$ content of from 28%, at a starting temperature of 33° C., to 22.3%, at a starting temperature of 80° C., are employed.

8. A process according to claim 7, wherein a starting temperature below 65° C. and a reaction temperature above 65° C. is employed, which temperature is reached utilizing the heat of reaction.

9. A process according to claim 8, wherein the reaction is initiated at ambient pressure and thereafter is conducted at pressure of 1.0 to 2.3 bar.

* * * * *